United States Patent [19]

Okada et al.

[11] Patent Number: 4,488,248
[45] Date of Patent: Dec. 11, 1984

[54] PARTICLE SIZE DISTRIBUTION ANALYZER

[75] Inventors: Tokuhiro Okada, Kakogawashi; Masayoshi Hayashi, Kobe; Hideaki Matsumoto, Takasagoshi, all of Japan

[73] Assignee: Toa Medical Electronics Co., Ltd., Kobe, Japan

[21] Appl. No.: 448,429

[22] Filed: Dec. 10, 1982

Related U.S. Application Data

[63] Continuation-in-part of Ser. No. 213,223, Dec. 5, 1980, abandoned.

[51] Int. Cl.³ ............................................. G06F 15/42
[52] U.S. Cl. ...................................... 364/555; 377/11
[58] Field of Search ................... 364/555; 377/11, 12; 324/71 CP

[56] References Cited

U.S. PATENT DOCUMENTS

| | | | |
|---|---|---|---|
| 3,390,229 | 6/1968 | Williams | 377/11 X |
| 3,810,011 | 5/1974 | Coulter et al. | 324/71.1 |
| 3,812,335 | 5/1974 | Coulter et al. | 364/555 |
| 3,935,562 | 1/1976 | Stephens | 377/11 X |
| 3,973,189 | 8/1976 | Angel et al. | 364/571 X |
| 4,071,891 | 1/1978 | Barrows | 364/555 X |
| 4,110,604 | 8/1978 | Haynes et al. | 377/11 X |
| 4,192,005 | 3/1980 | Kurtz | 364/558 X |
| 4,240,107 | 12/1980 | Yoshida | 377/11 X |
| 4,309,757 | 1/1982 | Frey et al. | 364/555 X |

Primary Examiner—Edward J. Wise
Attorney, Agent, or Firm—Lucas & Just

[57] ABSTRACT

A particle size distribution analyzer comprising a particle detector adapted to produce signals in response to the sizes of particles by electrical or optical differences between a liquid and the particles dispersed therein, a plurality of comparators connected in parallel to said particle detector for producing pulses in correspondence with said signals, counters connected to each of said comparators for counting said pulses, a data input/output unit connected to each individual counter, whereby said input/output circuit receives signals sent in parallel from said counters, a keyboard unit connected to said input/output circuit operative to enable various conditions to be input from the outside, a central processing unit circuit, a read only memory and, a random access memory connected to said later input/output unit for statistically processing the pulse received, and a data output unit connected to said data input/output unit, said data output unit including at least a recorder.

8 Claims, 52 Drawing Figures

FIG.9a PV
FIG.9b MIP
FIG.10a PV
FIG.10b MIP

FIG.9c MAP
FIG.9d DW
FIG.10c MAP
FIG.10d DW

FIG.9e H-W
FIG.9f MEA
FIG.10e H-W
FIG.10f MEA

FIG.9i MED
FIG.9j MID
FIG.10i MED
FIG.10j MID

PARTICLE SIZE DISTRIBUTION ANALYZER

This is a continuation-in-part of application Ser. No. 213,223 filed Dec. 5, 1980, now abandoned.

The present invention relates to a particle size distribution analyzer for obtaining various data through the analysis of the size distribution of particles, particularly microscopic particles, such as blood cells, wherein the particles are dispersed in a liquid. More particularly, the present invention relates to a particle size distribution analyzer which cannot only obtain data with respect to particle size distributions but also can obtain statistically processed data on the basis of distribution graphs, thereby ensuring an accurate, speedy, high precise analysis of particle size distributions.

It is commonly known in the art to utilize differences in electrical impedance between the liquid and the particles dispersed therein to detect the particles, as particle-dispersed liquid is passed through a pore. It is also known, in such cases, that the strength of signals is proportional to the size of the individual particles. Utilizing this fact various data on the size of particles are obtained, for example, for use in the clinical purposes.

In analyzing blood cells commonly the blood is diluted 50,000 times with a physiological saline solution, and its concentration is reduced to about 100 cells/mm$^3$. Blood normally contains about 50,000 cells per cubmic millimeter. After the dilution takes place, the measurements are performed cell by cell on about 25,000 cells. The series of measurements are completed in about 10 seconds, which on the average means that one cell is measured in about 0.4 millisecond. So long as the measurement is completed at such a speed, a microcomputer can be employed to ensure a simplified data processing. However, problems arise from the uneven distribution of particles dispersed in a liquid. For instance, as generally known, such problems arise in a blood cell counter when two or more cells pass through the counter at one time. This tends to cause miscounting. Previous attempts to solve the problem have concentrated the shape of the pore and the speed at which the particles pass therethrough as the decisive factors.

When the size of the particles to be analyzed is approximately 100-micron, it is the common practice to use a 100-micron diameter pore and to adjust the passing speed to a few meter per second. Under this condition signals are emitted at intervals ranging from a few microseconds to a few hundredths of a microsecond. If a high-speed A-D converter is to be employed for singling out the particles by their sizes and converting the signals into digits, the converter must be of such high-speed as to complete the series of operations in microseconds and then stop until subsequent signals arrive. Such converters are very expensive so that the cost of a device using such is very expensive. This has also been found to be uneconomical in light of the average particle density.

There is another method in which a plurality of relatively simple counters are arranged in parallel and wherein the thresholds of measured values sensed by each counter are changed by degrees so as to allow a single detector to detect all the particles. The detected results are numerically classified and then the data obtained are analyzed. This technique requires each counter to have a wide counting range. Accordingly, the size of the counter necessarily becomes large. In addition, to increase the degree of precision, a number of counters must be employed. This will also inevitably be reflected in the cost.

The present invention is directed toward solving the problems pointed out above with respect to the prior art analyzing system of particle size distribution, and has for its object to provide an improved particle size distribution analyzer capable of highly precise and speedy analysis.

Another object of the present invention is to provide an improved particle size distribution analyzer capable of data processing and statistical analysis of particle size distribution graph.

Other objects and advantages of the present invention will become apparent from the following description given hereunder; it should be understood, however, that the detailed description and specific embodiments are given by way of illustration only, since various change and modifications within the spirit and scope of the invention will become apparent to those skilled in the art from this description.

SUMMARY OF THE INVENTION

According to the present invention, a particle size distribution analyzer includes a particle detector adapted to produce signals in response to the sizes of the particles detected by electrical or optical differences between a liquid and the particles dispersed therein, a plurality of comparators connected in parallel to said particle detector, and counters connected to each of said comparators. A data input/output unit is connected to said individual counters for receiving signals sent in parallel from the counters. A keyboard unit is also connected to said data input-output unit to enable various parameters such as frequency range and cursor location to be input from the outside. A central processing unit processes the data in accordance with programs stored in a read only memory the processed data being stored selectively in a random-access memory. The results may be printed or displayed on a display unit.

DETAILED DESCRIPTION OF THE INVENTION

Figure 1:
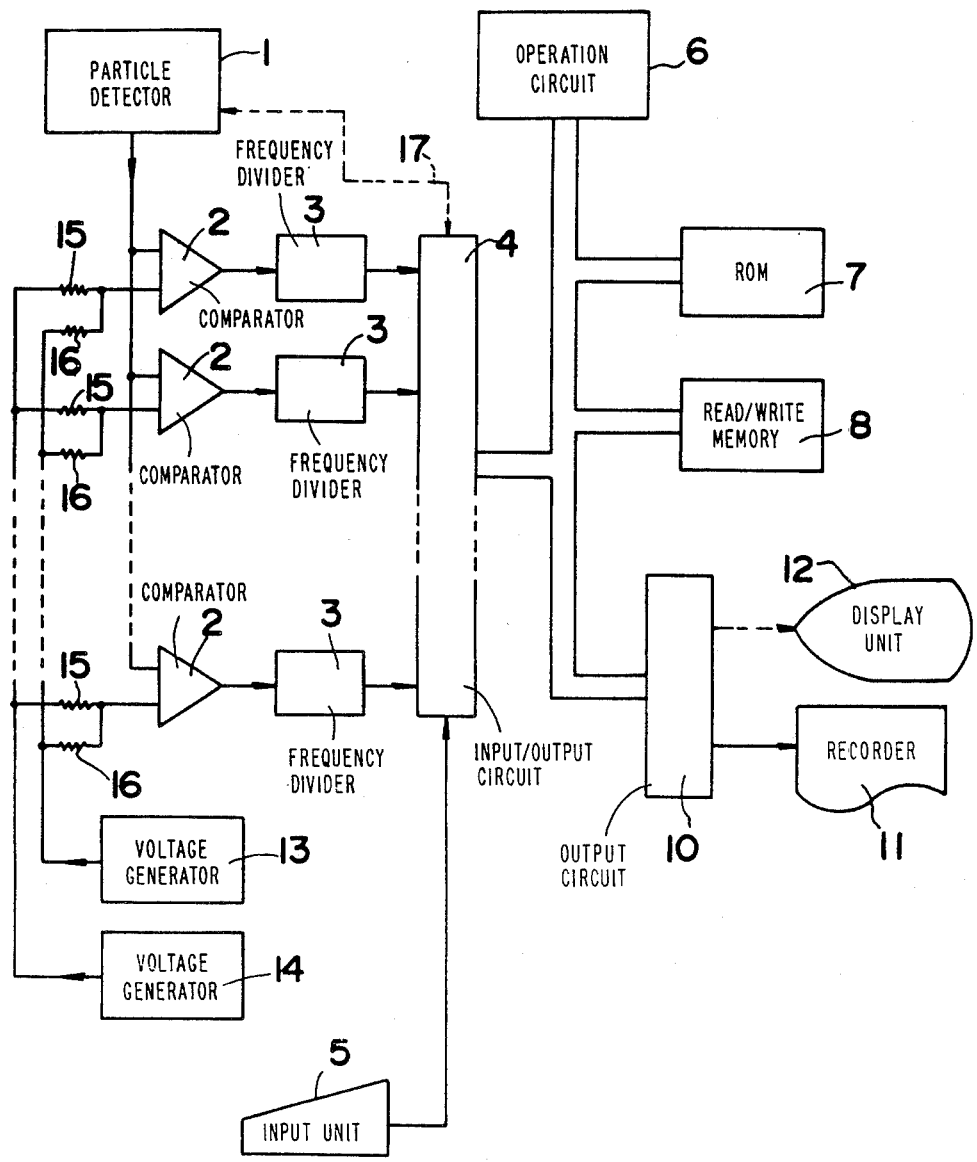
FIG. 1 is a block diagram of a system in accordance with the present invention.

Referring to FIG. 1, the reference numeral 1 designates a particular detector of the type well known in the art and adapted to detect particles by electric or optical differences between the particles and the suspension and to produce signals whose strength depends upon the sizes of the individual particles. In the preferred embodiment of a liquid containing dispersed particles, such as blood cells, is passed through a conventional pore, and the particles are detected by differences in electrical impedance between the suspension and the particles.

The detector 1 is connected to a plurality of conventional comparators 2 provided in parallel. Each of the comparators 2 is connected to a corresponding counter 3.

Output signals produced by the particle detector 1 are applied to the comparators 2. The strength of the individual signals depend upon the volume of each detected particle. Normally 50 to 100 comparators are arranged in parallel; accordingly each comparative voltage will consist of a fraction of 1/50 to 1/100 output depending upon the number of the comparators. Commonly, signals are emitted at intervals of 100 microseconds from the particle detector 1, but it will be appreciated that the intervals cannot be constant. It sometimes happens that the signals are sent with almost no interval between one and the next. To effect the analysis of each signal, therefore, there would be required a digital circuit having an operational speed of the order of a few microseconds.

In accordance with the invention, the counters 3 are provided in parallel in correspondence to each comparator 2. The counter 3 has a frequency-dividing ratio falling in the decimal-to-centennial range. For best results, the counters 3 are designed so as to approximately equalize the pulse intervals and to slow down the rate to the point that a conventional CPU can be utilized. Suitable counters are readily available, the only criterion is that they be able to produce a single pulse in response to 100 input pulses. The counters 3 are arranged to input in parallel to the data input/output unit 4.

Further in accordance with the invention, the pulse signals sent in parallel from the counters 3 are equalized and fractionalized, and the signals constitute, point to point, the area below a curve forming a cumulative particle size distribution graph. When the points cumulate, a cumulative distribution graph is formed. For best results, the data input/output unit 4 additionally receives signals through a path 17 with respect to the quantity of the particle-dispersed liquid. This measurement requirement, of course, depends upon whether the analysis is to be based upon the analysis of a given quantity of the particle-dispersed liquid, or on the counting time, or on the counting of the number of particles. Commonly, for instance, the number of red cells in blood is measured, and therefore, a one-time measurement for the analysis of the particles in a given volume is required. For such measurements, a suction analysis is performed with respect to a given amount of particle-dispersed liquid.

However, in other cases when particles are less dense per unit volume, or when the distribution of particles is uneven as is usual in the industrial field, it may be desirable to continue the analysis until the number of detected particles increases to a statistically significant number. Otherwise, the data obtained will lack accuracy. And when it is required to observe changes in the distribution curve with time through repeated measurements, it may be more desirable to perform short-term measurements for a standard interval or, as for the rate of dissolving of blood with the addition of saponins.

Preferably, the data input/output unit 4 receives signals from keyboard unit 5 so that various conditions can be set from the outside, for example, the type of measurement selected as mentioned above or the range of particle sizes to be analyzed. The data input/output unit 4 is electrically connected to a central processing unit (CPU) 6, the data being converted into the proper format for the CPU 6 to enable it to properly process it in conventional manner, It will be appreciated that such techniques are well known in the art and consequently will not be described here.

Further, the data input/output circuit 4 is connected as well known in computer art to CPU 6, read-only memory (ROM) 7 random-access memory (RAM) 8 and data output unit 10.

The data input/output unit 4, the CPU 6, the ROM 7, and the RAM 8 all make up a standard computer assembly, many types of which are available on the commercial market. The selection of a particular computer may be made by any skilled person in the art. The ROM is of course typically used for storing the program for operation and the RAM is used to store the data.

The data output circuit 10 is further connected to a recorder 11, and where necessary, to a display unit 12. It is also seen that each of the comparators 2 is provided with voltage divider resistances 15 and 16 which provide a comparative voltage to the comparator 2 when voltage is applied from reference voltage generators 13 and 14.

Figure 2:
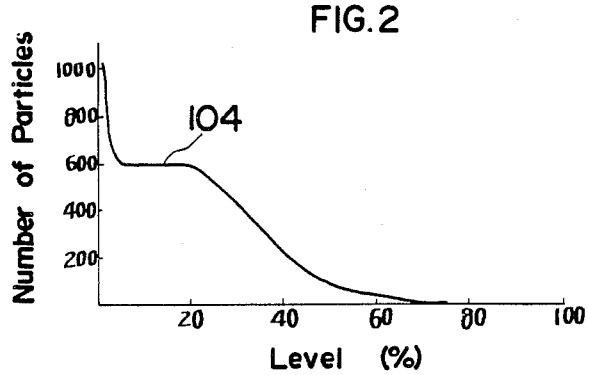
FIG. 2 is a graph showing an example of the cumulative particle size distribution.

FIG. 2 shows an example of a typical cumulative particle size distribution curve, which is obtainable in accordance with the invention as follows:

The data input/output unit 4 receives pulses sent from the counters 3; suitably, at the rate of one pulse per 100 particles. In response to the input of each pulse the CPU 6 calls the number stored in the RAM 8 corresponding to the appropriate address, and adds one thereto. Then the augmented number is again written in the memory. This procedure is repeated until the desired measurement is complete. As referred to above, the measurement is completed optionally on the basis of volume, time or particle number. As shown in Table 1, each address has its appropriate number of particles (cumulative value) stored:

TABLE 1

| Address | 1 | 2 | 3 | 4 | 5 | 6 | 7 | 8 | 9 | 10 |
|---|---|---|---|---|---|---|---|---|---|---|
| 00 | 1454 | 832 | 698 | 641 | 619 | 608 | 604 | 602 | 599 | 596 |
| 10 | 596 | 597 | 597 | 596 | 596 | 597 | 596 | 594 | 590 | 586 |
| 20 | 580 | 571 | 559 | 542 | 524 | 503 | 480 | 457 | 431 | 405 |
| 30 | 383 | 362 | 341 | 320 | 300 | 280 | 261 | 244 | 227 | 211 |
| 40 | 196 | 184 | 171 | 159 | 148 | 136 | 126 | 117 | 108 | 99 |
| 50 | 92 | 86 | 79 | 72 | 66 | 61 | 56 | 52 | 47 | 43 |
| 60 | 39 | 35 | 33 | 30 | 27 | 25 | 22 | 20 | 18 | 16 |
| 70 | 14 | 13 | 12 | 10 | 9 | 8 | 8 | 7 | 6 | 6 |
| 80 | 5 | 5 | 4 | 4 | 4 | 4 | 3 | 3 | 3 | 3 |
| 90 | 3 | 2 | 2 | 2 | 2 | 2 | 2 | 1 | 1 | 1 |

For instance the Address (1) has the number 1454; the Address (10) has the number 596; the Address (55) has the number 66, each of these numbers denoting the sum of particles measured in a particular range. After completing the measurement, the CPU 6 calls each address progressively, and the called numbers are recorded through the data output unit 10 by the recorder 11. The resulting cumulative particle size distribution curve using the raw data is depicted as shown in FIG. 2.

A first operation which may be performed on the data is to determine the differences between numbers of particles for adjacent particle sizes. Table 2 has been obtained by tabulating differences between each two adjacent addresses.

TABLE 2

| Address | 1 | 2 | 3 | 4 | 5 | 6 | 7 | 8 | 9 | 10 |
|---|---|---|---|---|---|---|---|---|---|---|
| 00 | 622 | 134 | 57 | 22 | 10 | 5 | 2 | 3 | 3 | 0 |
| 10 | 1 | 0 | 1 | 0 | 1 | 1 | 2 | 4 | 4 | 6 |
| 20 | 9 | 12 | 17 | 18 | 21 | 23 | 23 | 26 | 26 | 22 |
| 30 | 21 | 21 | 21 | 20 | 20 | 19 | 17 | 17 | 16 | 15 |
| 40 | 12 | 13 | 12 | 11 | 12 | 10 | 9 | 9 | 9 | 7 |
| 50 | 6 | 7 | 7 | 6 | 5 | 5 | 4 | 5 | 4 | 4 |
| 60 | 4 | 2 | 3 | 3 | 2 | 3 | 2 | 2 | 2 | 2 |
| 70 | 1 | 1 | 2 | 1 | 1 | 0 | 1 | 1 | 0 | 1 |
| 80 | 0 | 1 | 0 | 0 | 0 | 1 | 0 | 0 | 0 | 0 |
| 90 | 1 | 0 | 0 | 0 | 0 | 0 | 1 | 0 | 0 | 0 |

Figure 3:
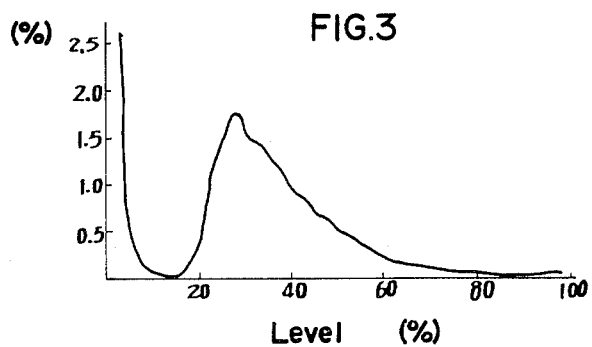
FIG. 3 is a graph showing differences in the number of particles among the addresses in FIG. 2.

In Table 2 the difference between the figures of the Addresses (1) and (2) is written in the Address (1), and the other figures are likewise written. The graph shown in FIG. 3 is depicted using these differences. That is, the graph has been obtained by simultaneously reading out the adjacent two addresses in the RAM 8 and performing a subtraction. The actual figures in Table 2 may also be displayed on the display unit 12 if desired where necessary.

The foregoing general description is concerned with a single type specimen, but the analyzer according to the present invention is useful for many kinds of analysis and types of specimens and these will be described in more detail with reference to examples.

EXAMPLE 1

The RAM 8 is provided with three areas of addresses which will be designated by memory No. 1, memory No. 2 and memory No. 3.

In memory No. 1 the counts of each number of particles as shown in Table 1 is assigned to each address. Preferably several sets of these are stored.

In memory No. 2, the differences as shown in Table 2, are stored in each address either as the figures, or as the quotients of these numbers over the total number of particles in %. Preferably, several sets of this are also stored.

For best results, the memory No. 3 is used for temporal memory so as to effect in known manner the scanning of drawings and graphs from the top downwards in accordance with a specified scanning order, when the data are displayed or recorded by the display unit 12 and the recorder 11. This eliminates the necessity of calling each curve separately when two or more curves are to be overlappingly depicted or recorded. It will also be appreciated that this diminishes the work of inserting a number of papers into a printer.

Figure 4:
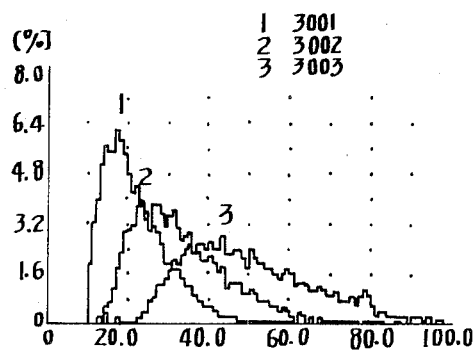
FIGS. 4 to 10 are graphs showing the results of measurement.
Figure 5:
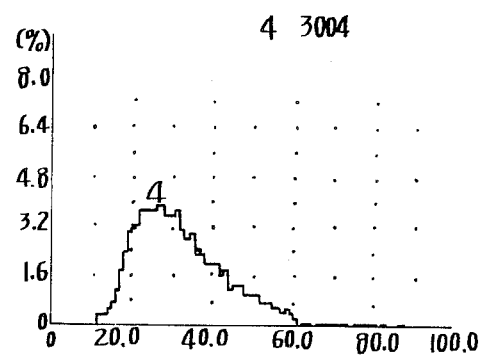

An example of measured results are shown in FIGS. 4 and 5, where the curves refer to particular specimens designated 3001, 3002, 3003 and 3004.

EXAMPLE 2

Figure 6:
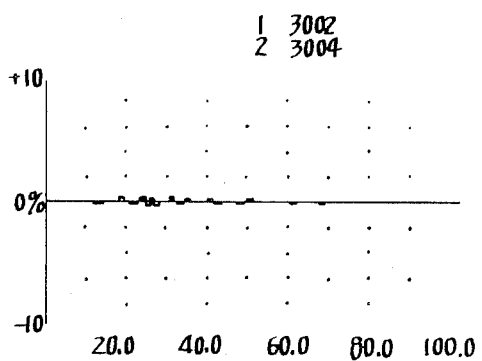

The remaining addresses of the RAM 8 are alloted as memory No. 4. For further analysis, specimens such as Nos. 3002 and 3004 are input to the keyboard unit 5, so that the differences between the two particle size distributions may be read. In accordance with the program each percentage value in each address is called in the operational order programmed in the ROM 7, and of course each of these percentage values correspond to the contents stored in the memory No. 2. Then, the percentage value of each particle size in the 3004 distribution is from that in the 3002 distribution. The differences obtained in this way are stored in each address in the memory No. 3. Finally, the contents of the memory No. 3 are scanned in the scanning order specified in the display unit 12 (or recorded in the recorder 11). In this way the results are progressively displayed (or recorded). FIG. 6 has been obtained in this way. Preferably, the scales and figures are simultaneously recorded from the top downwards by a stylus printer.

Figure 7:
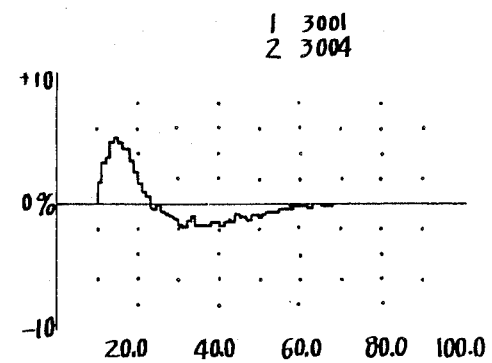
Figure 8:
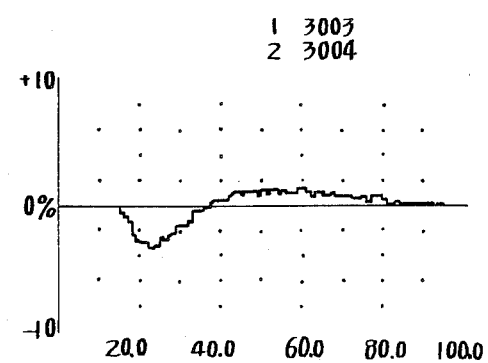

FIGS. 7 and 8 were obtained in the same manner as described above, but with respect to the specimens Nos. 3001 and 3004, and Nos. 3003 and 3004, respectively. As is evident from these examples, the specimen No. 3004 is used as the reference specimen. It will be appreciated from these graphs that in the case of FIG. 7 the small size is predominant while the case of FIG. 8 the large size is predominant. This tendency of course can be seen in FIG. 4.

More specifically, in FIGS. 4 and 5 the red cells of a patient suffering from microcytic hypochromic anemia are used for specimen No. 3001 designated by Curve (1); those of a normal person are for specimen No. 3002 designated as Curve (2); and those of a patient suffering from microcytic normochromic anemia are used for specimen No. 3 designated by Curve (3). In FIG. 5 the Curve 4 shows specimen No. 3004 used as the reference. Extreme samples have been especially selected as specimens, so as to clearly indicate differences among them.

TABLE 3

| | Items of computation | Symbols | | Contents |
|---|---|---|---|---|
| 1 | PEAK VALUE (Peak value ; particle size dimension) | PV |  | Largest number of particle sizes |
| 2 | MIN. PARTICLE (Minimum particle volume) | MIP |  | Minimum particle volume |
| 3 | MAX. PARTICLE (Maximum particle volume) | MAP |  | Maximum particle volume |
| 4 | DISTRI. WIDTH (Particle distributation width) | DW |  | Particle distribution MAP − MIP = DW |

TABLE 3 (Continued)

| | | | | |
|---|---|---|---|---|
| 5 | HALF-WIDTH (Half value particle width) | H-W |  | Particle width at a 1/2 value of the height |
| 6 | MEAN (Mean volume) | MEA |  | Mean particle volume<br>TV/NT = MEA |
| 7 | VOL. RATIO (Volume ratio) | VR |  | Ratio between the total volume on the right and that on the left of the peak value line<br>$\sum_{B}^{A} Volume / \sum_{A}^{C} Volume = VR$ |
| 8 | TOTAL VOL. (Total volume) | TV |  | Total volume of the particles measured between B & C |
| 9 | MEDIAN (Median area value) | MED |  | Median area value, which divides the total dimension into two equal parts on both sides of the line |
| 10 | MIDRANGE (Particle width center value) | MID |  | Center value of particle distribution<br>DW/2 + MIP = MID |
| 11 | AREA RATIO (Area ratio) | AR | 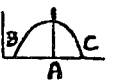 | Ratio between the area on the left and that on the right with respect to the peak value line<br>$\sum_{B}^{A} Area / \sum_{A}^{C} Area = AR$ |
| 12 | TOTAL AREA (Total area) | TR |  | Total number of particles shown on the total area diagram |
| 13 | COUNT (Number of particles) | CNT | | The number of particles set by the count level |
| 14 | VOLUME (Volume ratio) | VO | HT value in the blood cells 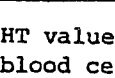 | Area x Compensation value = VO |
| 15 | MPV | MPV | MCV value in the blood cells<br>VO/CNT = MPV | |
| 16 | HEIGHT/WIDTH | H/W | 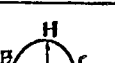 | Height divided by particle width<br>H/DW = H/W |
| 17 | HEIGHT | H |  | Height at the peak value particle volume |
| 18 | LEVEL RATIO (Level ratio) | LR | 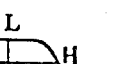 | L level    CNT Value<br>H level    Set value<br>L/H x 100 = LR |

EXAMPLE 3

Various arithmetical operations may be performed to obtain the parameters given in Table 3 operations. The data thus obtained are shown in FIGS. 9 and 10.

In this example, the changes with time various parameters with respect to the particles, such as blood cells, are observed and the data are simultaneously recorded under each item. The same specimen is continuously measured 20 times at the intervals of 5 seconds during which the time-changes of the parameters are observed from the initial stage. In this way the deviations from the initial value are measured.

The test is performed as follows:

Referring to FIG. 1, the detector 1 performs the measurements 20 times at the intervals of 5 seconds as conditioned, and the data obtained through the series of measurements are stored in the memory No. 1 as information about the particle size distribution. At the same time the data are stored in % in the memory No. 2. When the series of measurements are finished, deviations from the initial value (the result of the first measurement and operation) of each parameter listed in Table 3 are determined. The results are stored in the memory No. 4 for displaying and recording. In Table 3 the "PV" (the peak value of a particle size distribution curve) is obtained firstly by finding the thresholds of the peak value of each distribution curve in the memory No. 2, and then by storing the quotients of division of each measured value from the 2nd time onwards by the initial value (denominator). The count (CNT) at each measurement, the Hematocrit values (VO) in blood cells, and MPV corresponding to MCV can be simultaneously measured and be subjected to further arithmetical operations. These values are obtained directly from the memory No. 1, the operation performed and are stored in the memory No. 4.

Figure 9K:
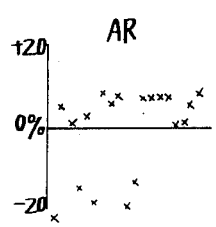
Figure 10K:
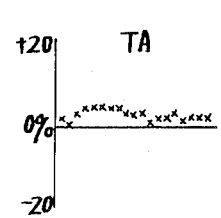
Figure 10K:
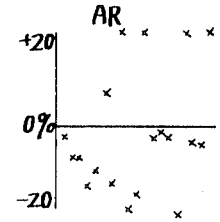
Figure 9M:
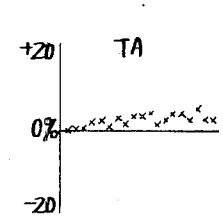
Figure 9M:
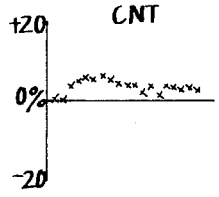
Figure 9N:
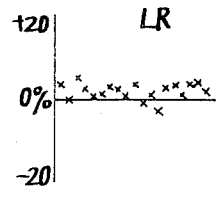
Figure 10M:
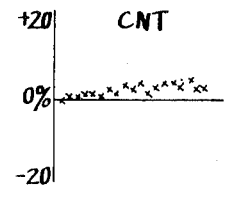
Figure 10N:
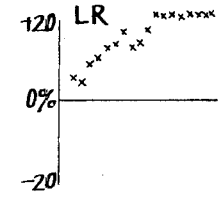
Figure 9O:
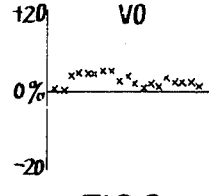
Figure 9P:
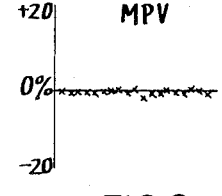
Figure 10O:
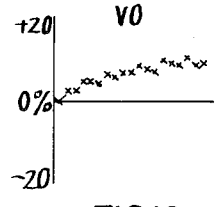
Figure 10P:
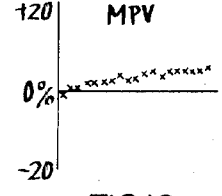
Figure 9Q:
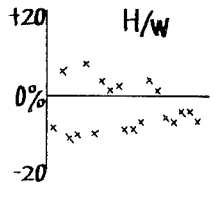
Figure 9R:
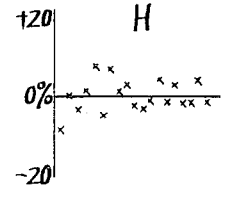
Figure 10Q:
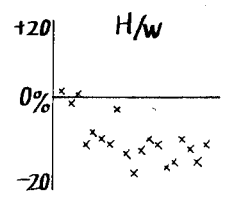
Figure 10R:
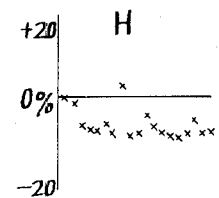

To give an actual example of measurement, FIGS. 9a to 9r and 10a to 10r are shown. FIGS. 9a to 9r have been obtained through the series of measurements of parameters with respect to the red cells in blood of a normal person, whereas FIGS. 10a to 10r have been obtained with respect to those of an icteric patient. It will be appreciated from FIGS. 10a to 10r that the red cells of the icteric patient changes with time, having a larger deviation. In addition, the particle size distribution is uneven.

It can be concluded, therefore, that if blood cells have any disease, it will be easily discovered through the measurement of a particle size distribution with respect to the patient's blood cells. This type of measurement is performed on blood having less density of cells compared with a normal cell-dispersed blood. If severer conditions are imposed upon the specimen of blood, for example by changing an osmosis pressure or pH value, clearer changes will be observed.

EXAMPLE 4

Figure 11:
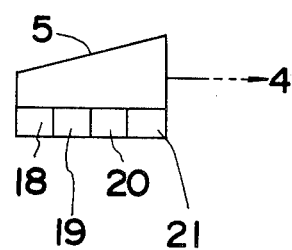
FIG. 11 is a schematic view of a modified version of the input unit.
Figure 12:
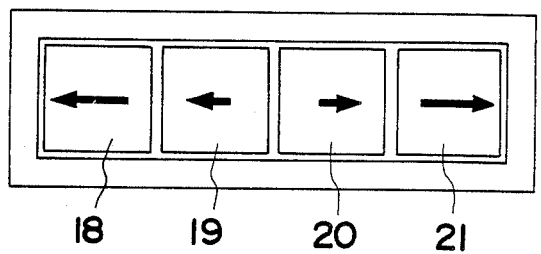
FIG. 12 is a schematic plan view of suitable press-button switches included in the input unit in FIG. 11.

As best seen in FIGS. 11 and 12, the keyboard unit 5 employed in the present invention is uniquely designed and constructed so as to enable the cursor 23 to be visually controlled in its location by actuating one of a set of keys. The operator can watch the movement of the cursor 23 appearing on the display screen. In addition to the conventional alphabetical and numeral keys commonly used in computers, the keyboard unit 5 has four specially designed keys 18 to 21.

The key 18, when actuated, enables the cursor 23 to shift to the left at high speed; the key 19 enables it to shift to the left at low speed; the key 20 enables it to shift to the right at low speed, and the key 21 enables it to shift to the right at high speed. The cursor 23 stops only when any of the keys 18 to 21 comes out of contact with the operator's finger.

The actuation of the keys 18 to 21 is signalled to the data input/output unit 4, and accordingly, the CPU 6 changes the data on the position of the cursor 23, the data being stored in the RAM 8. For example when the key 18 is actuated, a 10-step deduction is performed, and when the key 20 is actuated, the one-step addition is performed. Optionally, it will be appreciated that it is possible to modify the operation so as to effect the successive addition and deduction through the actuation of the keys 19, 20, or alternatively, it is also possible to modify the operation so as to effect only a step-by-step operation even if the keys are continuously oppressed.

By shifting the cursor, i.e. the cursor trace 23 in the display, various required conditions can be input for the arithmetic operations without the necessity for tedium and repetitious calculations on the part of the operator.

Figure 13:
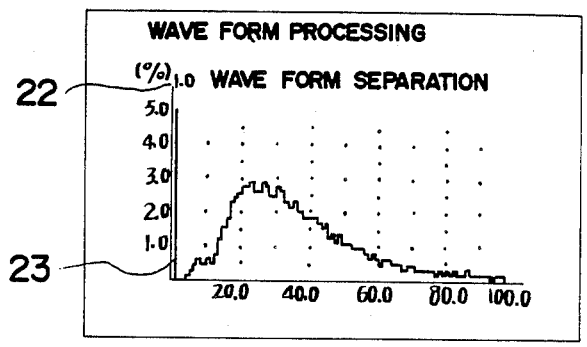
FIGS. 13 to 17 are graphs showing the modes of presentation provided by the display unit.
Figure 14:
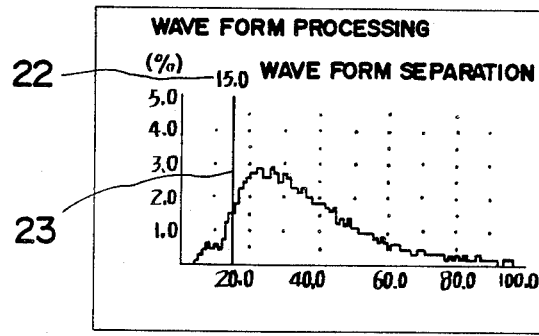

As described above, a particle size distribution calculated on a percentage basis is stored in memory No. 2. Various conditions for statistical arithmetic operations from the data are input in the following manner:

FIGS. 13 and 14 are obtained by processing wave forms by the method of least squares to make the data approximate a polynominal function, and thereafter indicating the function in graphs. In processing the wave forms, a prior designation of the portion of the curve should be established for the arithmetic operations. When two or more kinds of particles are present and are indicated by two peaks in the graph, this previous designation will be particularly essential. In such cases a separation of the curve is required.

Initial data is input through keyboard unit 5 so as to set an upper limit and a lower limit for effecting the wave form processing by the method of least squares, as well as the wave form separation therefor. The desired program for the arithmetic operation is called from the ROM 7, so that the cursor trace 23 and a numeral 22 indicating the position of the cursor trace appear on the display on which the distribution curve is being presented. Conveniently, the abscissae indicates percentage, and the first designated position is 1%, since the position 0% means that no designation is made. In order to shift the cursor trace 23, the button switches 18, 19, 20 and 21 are pressed. Rough adjustments may be made by the switches 18 and 21, and the final exact adjustment is made by the switches 19 and 20. In this way the cursor trace 23 is set as desired, by visual reference to the actual displayed curves, thereby ensuring the exact and easy locating thereof. This is particularly advantageous over the conventional numerical data input operation.

Figure 15:
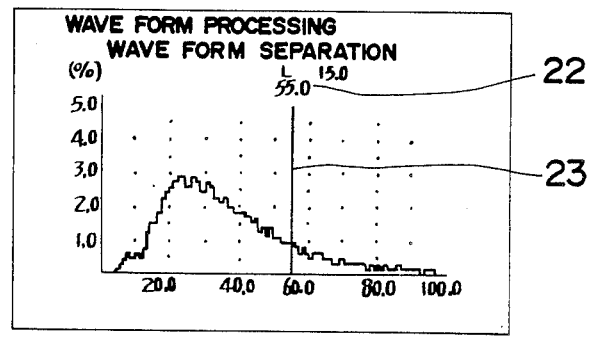
Figure 16:
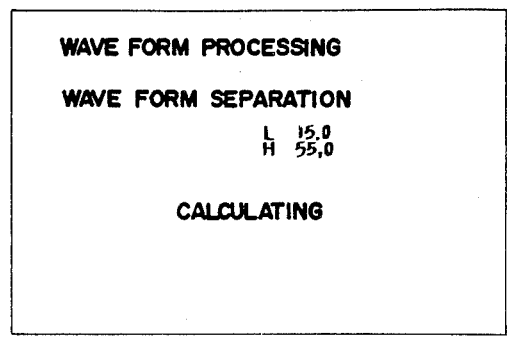
Figure 17:
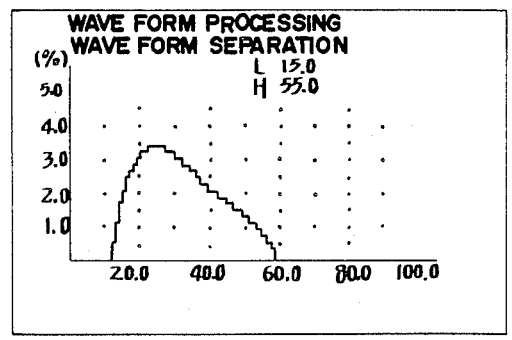

For instance, as shown in FIG. 14 the lower limit is set to 15%, and the upper limit is to 55% as shown in FIG. 15. The arithmetic operation is initiated and during this time there is suitably indicated on the display that the operation is under way. Upon completion, the display will indicate the curve which has been statistically processed on the basis of the polynominal function obtained in the above-mentioned manner.

To further simplify the operation, the calculations can be split, that is, first from the lower limit to the peak, and secondly, from the peak to the upper limit. During the operation it is normally required to find a single peak, but if two or more peaks of the same value are found or if the peak is rather flattened, the peaks obtained may not be sufficiently accurate and correction is needed. One of the advantages of the present invention is that the correction of peak values can be readily performed.

Figure 18:
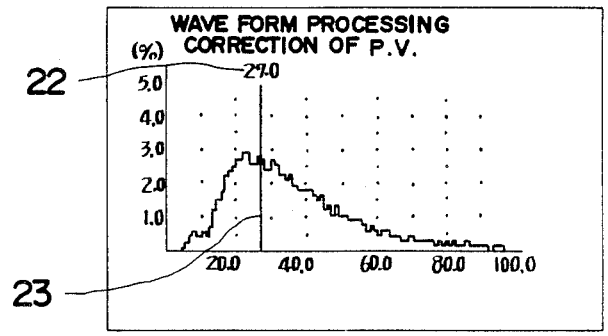
FIG. 18 is a graph showing another mode of operation in accordance with the present invention.

As shown in FIG. 18 data may be input into keyboard unit 5 so as to correct the peak value. The cursor trace 23 will again appear in the display, and the cursor trace is reset to the correct peak value by use of the button switches 18 to 21. The arithmetic operation is then reperformed on the basis of this corrected peak value. The data obtained are given in Table 4, which in accordance with the invention are stored in the memory No. 3 of the RAM 8. The data are also printed by the recorder.

TABLE 4

| PEAK VALUE | 27.0 | MIN. PARTICLE | 15.0 |
|---|---|---|---|
| MAX. PARTICLE | 59.0 | DISTRI. WIDTH | 45.0 |
| HALF-WIDTH | 21.0 | MEAN | 33.0 |
| VOL. RATIO | 0.306 | TOTAL VOL. | 22478 |
| MEDIAN | 32.0 | MID RANGE | 40.5 |
| AREA RATIO | 0.494 | TOTAL AREA | 648 |
| COUNT | 681 | LEVEL RATIO | 13.07% |
| VOLUME | 60.2% | MPV | 88.4 |
| HEIGHT/WIDTH | 0.93 | HEIGHT | 4.17% |

Preferably the recorder 11 is adopted to record not only the data mentioned above but also the graphs presented in the display. Such recorders are readily available commercially.

As described above, various conditions required for arithmetic operations can be input by merely adjusting the positions of the cursor trace 23 in the display by visual reference to the curve, thereby ensuring an accurate, simple and speedy operation. This is tremendously advantageous over the conventional numerical data input operation.

When it is desired that a part of the display be magnified, an upper and a lower limit to the magnification can be input, by shifting the upper and lower cursor traces along with appropriately changing the onputs from keyboard unit 5.

The particle size distribution analyzer according to the present invention can be applied not only to the medical field but also to other fields, such as food processing. In food processing the analyzer can be employed to examine the state of powder in a particular solvent, e.g. the state of its aggregation or the process of dissolving therein. Also, the analyzer is useful for observing whether or not the germs contained in a particular food has been safely killed.

It will be understood that the claims are intended to cover all changes and modifications of the preferred embodiment of the invention, herein chosen for the purpose of illustration, which do not constitute departures from the scope and spirit of the invention.

What is claimed is:

1. A particle size distribution analyzer comprising a particle detector adapted to produce signals in response to the sizes of particles by electrical or optical differences between a liquid and the particles dispersed therein, at least one reference voltage generator which produces a signal, a plurality of comparators connected in parallel to said particle detector and to said reference voltage generator, said comparators comparing the signal from said particle detector to the signal from said reference voltage generators and producing pulses in correspondence with said comparison, counters connected to each of said comparators for counting said pulses produced from said comparators, an input/output circuit which receives signals sent from said counters, an input unit connected to said input/output circuit operative to enable pre-selected conditions to be input from the outside, a computer assembly connected to said input/output circuit, said computer assembly comprising a central processing unit, a read only memory, and a random access mamory, a data output circuit connected to said computer assembly and at least one recorder connected to said output circuit.

2. A particle size distribution analyzer according to claim 1 further comprising of at least one display unit connected to said output circuit, and wherein said display unit has a cursor.

3. A particle size distribution analyzer according to claim 2 wherein said input unit is a keyboard, and said keyboard is provided with switches for shifting a cursor trace on the display unit.

4. A particle size distribution analyzer according to claim 1 wherein the random access memory has a plurality of memory areas for storage of information, said information being obtained from the central processing unit and the input/output circuit.

5. A particle size distribution analyzer as set forth in claim 4, wherein said plurality of memory areas comprises a first memory area, a second memory area, and a third memory area, said first memory area being for storing a cumulative particle size distribution of a plurality of specimens, said second memory area being for storing the particle number distributions or particle size distributions represented in percent with respect to said plurality of specimens said percentage being the ratio of the number of particles at a specific size to the total number of particles wherein the ratio of the total number of particles to the total number of particles is 100%, and said third memory area being available for storing information said information in said third area being that information which will be displayed on a display unit or recorded by said recorder.

6. A particle size distribution analyzer as set forth in claim 4, wherein said plurality of memory areas includes a first memory area, a second memory area, a third memory area and a fourth memory area, said first memory area being operative for storing a cumulative particle size distribution of a plurality of specimens, said second memory area being operative for the storage of a particle number distributions or particle size distributions represented in percent said percentage being the ratio of the number of particles at a specific size to the total number of particles wherein the ratio of the total number of particles to the total number of particles is 100%, said third memory area being operative for holding information said information in said third memory area being that information which will be displayed on said display unit or recorded by said recorder unit, and said fourth memory area being for storing the difference in the particle size distribution between different specimens among said plurality of specimens.

7. A particle size distribution analyzer as set forth in claim 4, wherein said plurality of memory areas includes a first memory area, a second memory area, a third memory area, and a fourth memory area, said first memory area being operative for storing a cumulative particle size distribution of a plurality of specimens, said second memory area being for storing the particle number distributions or particle size distributions represented in percentages said percentage being the ratio of the number of particles at a specific size to the total number of particles wherein the ratio of the total number of particles to the total number of particles is 100%, said third memory area being operative for holding information said information in said third memory area being the information which will be displayed on said display unit or recorded by said recorder unit, and said fourth memory area being for storing deviations of parameters obtained through repeated measurements of the named specimen, said deviation being the difference between the initial values of the specimens wherein the specimen is continuously measured twenty (20) times in intervals of five (5) seconds.

8. A particle size distribution analyzer as set forth in claim 4, wherein said plurality of memories includes a first memory area, a second memory area, and a third memory area, said first memory area being for storing a cumulative particle size distribution, said second memory area being operative for storing the particle number distributions or particle size distributions represented in percentages said percentage being the ratio of the number of particles wherein the ratio of the total number of particles to the total number of particles is 100%, and said third memory area being operative for storing the results of arithmetic operations and distribution curves derived from said arithmetic operations, said arithmetic operations being particle size distribution curves approximated in polynomial functions by the method of least squares, and said curves representing timely changes occurring in each of the eighteen (18) items listed in Table 3 of the application and wherein various conditions required for the arithmetic operation are input by positioning of the cursor on the display.

* * * * *